(12) United States Patent
Zare et al.

(10) Patent No.: US 6,768,548 B2
(45) Date of Patent: Jul. 27, 2004

(54) PULSE-BY-PULSE CAVITY RING-DOWN SPECTROSCOPY

(75) Inventors: Richard N. Zare, Stanford, CA (US); Andrew Shaw, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 528 days.

(21) Appl. No.: 09/775,689

(22) Filed: Feb. 1, 2001

(65) Prior Publication Data

US 2002/0101592 A1 Aug. 1, 2002

(51) Int. Cl.$^7$ ............................................... G01N 21/00
(52) U.S. Cl. ............................................................ 356/432
(58) Field of Search ................................. 356/432–445, 356/451, 519; 250/337.12

(56) References Cited

U.S. PATENT DOCUMENTS

| 5,912,740 A | 6/1999 | Zare et al. |
| 6,084,682 A | 7/2000 | Zare et al. |
| 6,094,267 A | 7/2000 | Levenson et al. |
| 6,392,753 B1 * | 5/2002 | Logunov ..................... 356/519 |

* cited by examiner

*Primary Examiner*—Tu T. Nguyen
(74) *Attorney, Agent, or Firm*—Lumen Intellectual Property Services, Inc.

(57) ABSTRACT

A cavity ring-down spectroscopy system and method is provided for detecting and resolving the ring-down pulse-by-pulse. The pulse-by-pulse cavity ring-down spectroscopy system enables for measuring absorption spectra of rapidly evolving systems on the order of the roundtrip time. The pulse-by-pulse analysis of ring-down profiles enables non-exponential ring-down absorption dynamics to be determined.

39 Claims, 5 Drawing Sheets

PULSE-BY-PULSE CAVITY RING-DOWN SPECTROSCOPY

STATEMENT REGARDING FEDERALLY SPONSORED RESEARCH OR DEVELOPMENT

This invention was supported in part by grant number N00014-00-1-0364 from the Office of Naval Research. The U.S. Government has certain rights in the invention.

FIELD OF THE INVENTION

The present invention relates generally to cavity ring-down spectroscopy. More particularly, the present invention relates to pulse-by-pulse cavity ring-down spectroscopy for measuring absorption spectra.

BACKGROUND ART

Cavity ring-down spectroscopy (CRDS) records the absorption spectrum of a species or sample inside an optical cavity by measuring the change in the ring-down lifetime as a function of wavelength. This technique is an advance over more traditional absorption techniques because CRDS is free of interference caused by fluctuations in the light source. The principles of the CRDS technique are well known and relatively simple. For a linear optical cavity, two mirrors are placed opposite one another forming a stable optical resonator cavity. Typically, a pulse of light enters the cavity through the back of one of the mirrors, bounces back and forth between the mirrors, and on each bounce some light emerges through the opposite mirror where it is detected. The losses of the cavity cause the intensity of the light to decrease exponentially as a function of time, and the ring-down is characterized by a lifetime $\tau$. For a typical 1-m cavity whose mirrors have a reflectivity of 99.99%, the time between bounces on the same mirror, which is called roundtrip time, is 7 ns, and the ring-down lifetime is 30 $\mu s$ during which time the pulse has traveled a distance of 5 km. When a sample is placed inside the cavity that absorbs at the wavelength of the light pulse radiation, the absorption constitutes an additional loss and the resulting ring-down lifetime is shortened. Measurement of the variation of $\tau$ with wavelength produces the absorption spectrum of the sample.

Typically, in CRDS several ring-down profiles are averaged together and a truncated portion of the ring-down wave form is fitted to an exponential to determine the ring-down lifetime or its reciprocal, which is called the ring-down rate. Such analyses, as they have been described in, for example, U.S. Pat. No. 6,094,267, U.S. Pat. No. 6,084,682, and U.S. Pat. No. 5,912,740, assume the sample concentration to be static and not to change during the averaging lifetime. As one skilled in the art readily acknowledges, resolving responses shorter than $\tau$ is difficult.

Accordingly, as one skilled in the art will readily acknowledge, it would be a major advantage in the art of CRDS to identify a structure and a method to detect and resolve ring-down events on a much shorter time scale.

OBJECTS AND ADVANTAGES

In light of the above, it is the primary objective of the present invention to provide a structure to detect and resolve ring-down at much shorter time scales using a method of pulse-by-pulse cavity ring-down spectroscopy.

It is another objective of the present invention to probe the temporal variation in the sample concentration on the order of the round-trip time rather than the ring-down lifetime.

It is yet another objective of the present invention to record each pulse and use the comparison of one pulse to the next to remove the effects of light intensity fluctuations.

It is still another objective of the present invention to observe ultra-fast processes inside the cavity and record real-time processes and chemical reactions.

The advantage of the present invention over the prior art is that pulse-by-pulse cavity ring-down spectroscopy allows measurement of absorption spectra of rapidly evolving systems including those for which the ring-down profile is non-exponential.

SUMMARY

These objects and advantages are attained by pulse-by-pulse cavity ring-down spectroscopy. More specifically, the present invention provides a structure and a method to detect and resolve the rate of ring-down pulse-by-pulse at a much shorter time scale than the ring-down lifetime $\tau$ by using pulse-by-pulse cavity ring-down spectroscopy. Accordingly, the present invention provides a structure and a method to measure absorption spectra of rapidly evolving systems. In fact, this method permits one to obtain the ring-down profile even in cases when that profile is non-exponential.

The invention further provides a pulse-by-pulse optical absorption apparatus that includes an optical cavity, a light source, a structure for time resolution, and a detector. The light source delivers a pulse into the optical cavity. The detector detects an intensity of at least one response pulse produced by the cavity in response to the pulse. In one embodiment, the response pulse involves a train of response pulses. The detector also includes a comparing device to compare at least two response pulses out of a train of response pulses.

The present invention also provides an ultra fast light source that delivers ultra short pulses into the cavity. Accordingly, the present invention provides an ultra fast detector that is able to detect at least one ultra short response. Furthermore, the present invention involves a structure for time resolution to resolve at least one ultra short response pulse. In one embodiment, this structure for time resolution includes a nonlinear medium for mixing at least one ultra short response pulse with a resolving pulse.

The present invention also provides a structure and method to manipulate the roundtrip time by changing the cavity length. Additionally, optical cavities capable of supporting a ring-down event include cavities provided by for instance input/output couplers, mirrors, gratings, or reflectors. Optical cavities include linear optical cavities as well as other (non-linear) types such as a ring cavity, a bow-tie cavity, a litman cavity, or other suitable cavities to include fiber optics as well as other light-guiding materials, within which ring-down can be observed. In each of these cavities, the cavity length is set at a predetermined value to resolve each response pulse at the detector.

Extension of the principles of pulse-by-pulse cavity ring-down analysis may be made to a continuous wave light source. Here temporal resolution of a continuous ring-down profile will yield similar information on the non-exponential decay dynamics. Furthermore, using a continuous wave light source, the analysis of pulse-by-pulse cavity ring-down spectroscopy could be extended and applied to cavity ring-up spectroscopy, whereby ring-up refers to the rate at which an optical cavity stores energy upon being irradiated.

BRIEF DESCRIPTION OF THE FIGURES

The objectives and advantages of the present invention will be understood by reading the following detailed description in conjunction with the drawings, in which:

FIG. 3b also shows an exponential fit to the intensity decay data.

DETAILED DESCRIPTION

Overview of Pulse-by-pulse Crds

Figure 1:
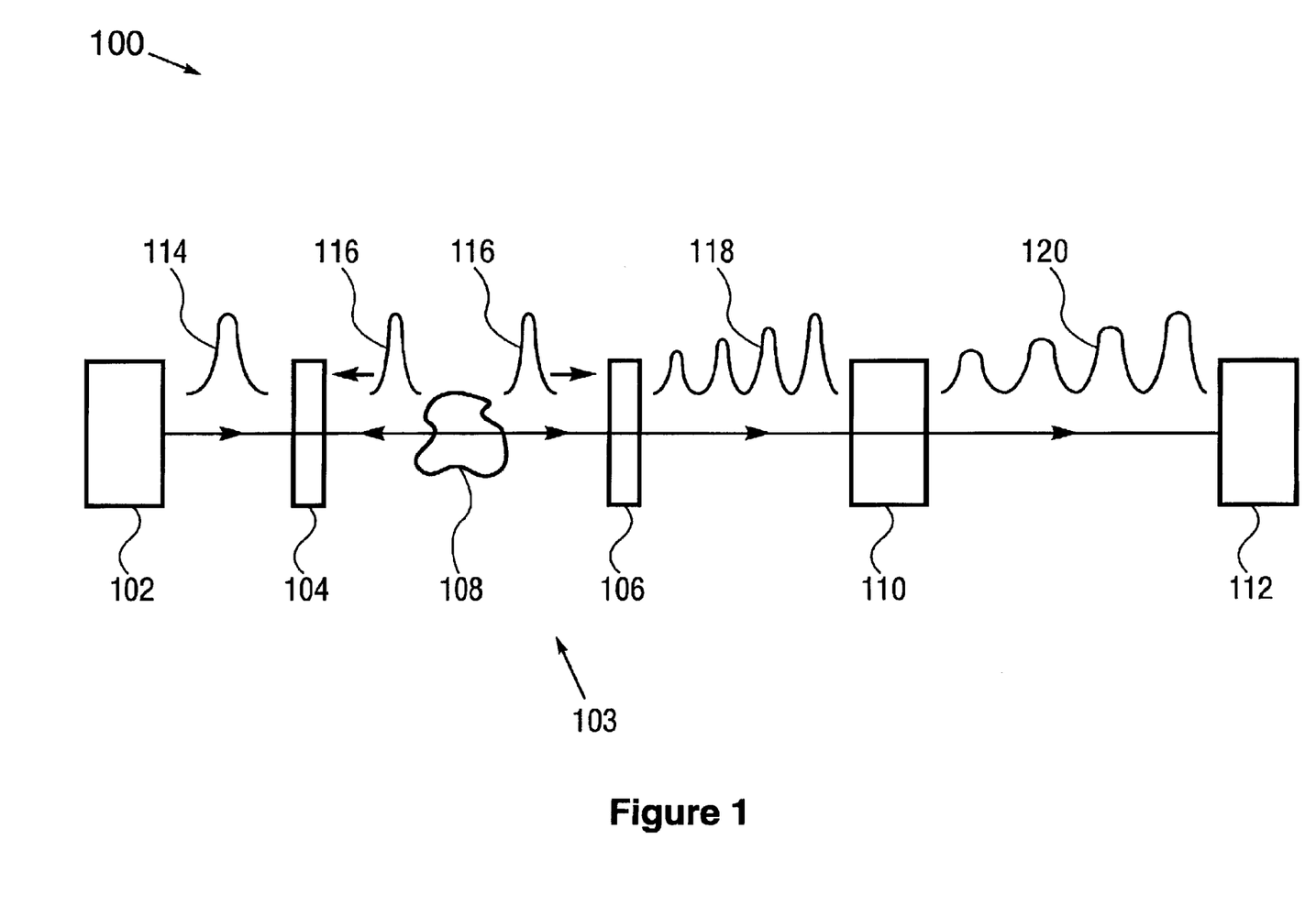
FIG. 1 is an overview of the system for pulse-by-pulse cavity ring-down spectroscopy.

The present invention provides a system and method for pulse-by-pulse cavity ring-down spectroscopy. FIG. 1 presents a schematic diagram of a pulse-by-pulse optical absorption system 100 according to the invention. An optical cavity 103 is provided that is capable of supporting a ring-down event. Optical cavities capable of supporting a ring-down event include cavities provided by for instance input/output couplers, mirrors, gratings or reflectors. Furthermore, optical cavities include linear optical cavities as well as other (non-linear) types such as ring cavities, bow-tie cavities, litman cavities, or other suitable cavities, to include fiber optics or other light-guiding materials, within which ring-down can be observed. In each of these cavities, the cavity length is set at a predetermined value to resolve each response pulse at a detector 112. In the exemplary embodiment of FIG. 1, two mirrors 104 and 106 delimit cavity 103; hence cavity 103 is a linear optical cavity. The linear distance between two mirrors 104 and 106, defining cavity 103, defines the length of linear cavity 103. In case of a non-linear cavity as described above with for instance multiple couplers, the cavity length is defined as the distance a single pulse will travel once between the couplers defining the cavity, i.e. the distance covered by a single pulse is one roundtrip.

A light source 102 delivers a pulse 114 into optical cavity 103. Typically, light source 102 is a laser capable of delivering a fast pulse 114 with a width on the order of femtoseconds, picoseconds, or nanoseconds. In the exemplary embodiment of linear optical cavity 103, pulse 114 enters cavity 103 through the back of mirror 104, which serves as the input coupler. A response pulse 116 results and is defined as the pulse produced by cavity 103 in response to pulse 114. Response pulse 116, bounces back and forth between mirror 104 and 106, and on each bounce some light emerges through the opposite mirror 106. The losses of the cavity 103 cause the intensity of the light to decrease as a function of time creating a pulse train 118. Pulse train 118 is the resulting ring-down profile produced by individual response pulses 116. In case of the presence of sample 108, pulse 114 is additionally attenuated and then impinges onto mirror 106. When sample 108 is placed inside cavity 103, the intensity of the light constitutes additional losses due to absorption by sample 108 at the wavelength of the light pulse radiation and the pulse train is shortened.

For pulse-by-pulse cavity ring-down spectroscopy it is the goal to resolve, measure intensity and analyze individual response pulses 116 one at a time. A structure for time resolution 110 is provided for viewing individual response pulses exiting optical cavity 103. The structure for time resolution 110 is an essential part of the present invention. A number of different structures for time resolution for all time scales are possible, all of which will provide single-pulse data acquisition and require a pulse-by-pulse non-exponential, analysis. For example, the structure for time resolution 110 can include a pulse stretcher, a heterodyne detection apparatus, a dispersive line, a time microscope, or other devices, which are capable of isolating and time resolving a single pulse and measuring its intensity. In the specific embodiment, pulse train 120 is the time resolved pulse train 118, which has been stretched out or magnified in time by structure for time resolution 110. In general, the present invention involves the isolation and time resolving of at least one response pulse exiting cavity 103. Consequently, at least one response pulse exiting cavity 103 could be a train of response pulses as indicated by pulse train 118.

At detector 112, which detects at least one time resolved response pulse it is the goal to analyze each individual response pulse 116 as it exited cavity 103 in a time domain and/or in a frequency domain. In addition, detector 112 compares and analyses at least two response pulses out of the train of response pulses. For instance, a streak camera, or equivalents thereof such as autocorrelation techniques, but not conventional electronic cascade devices, could be used for time domain imaging. A spectrometer, or equivalents thereof such as diffraction gratings, or indirect detection processes capable of converting a specific frequency dependent process into a countable detection event, could be used for frequency domain imaging. It is possible that structure for time resolution 110 is part of detector 112. This is the case when detector 112 is capable of single pulse data acquisition of individual response pulses 116 exiting cavity 103.

The principles of pulse-by-pulse cavity ring-down spectroscopy are readily generalized to various time regimes and are not limited to the femtosecond, picosecond, nanosecond or continuous time regime. In addition, the cavity length can be used to determine the time regime. For instance, a cavity length on the order of micrometers, millimeters and meters will set a time regime on the order of femtoseconds, picoseconds or nanoseconds respectively. To further illustrate the present invention, the following specific description provides a preferred embodiment with respect to femtosecond absorption dynamics of a sample 108 of simple liquids using short optical cavity lengths and roundtrip times.

Structures For Femtosecond Pulse-by-pulse Crds

Figure 2:
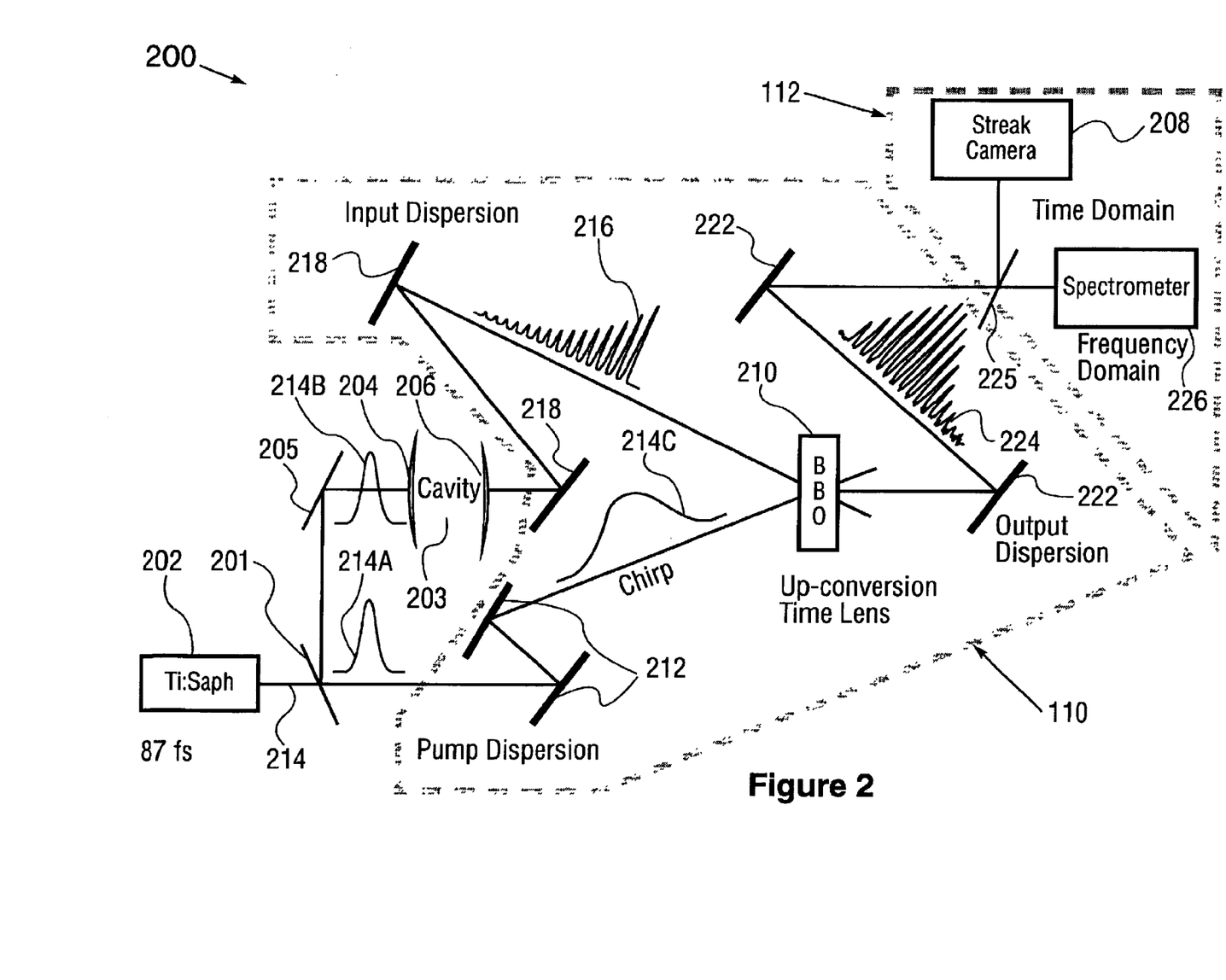
FIG. 2 illustrates an exemplary specific embodiment of the system for pulse-by-pulse cavity ring-down spectroscopy.

The preferred embodiment 200 as shown in FIG. 2 exploits a linear cavity delimited by two low-reflectivity mirrors 204 and 206 with reflectivities of 88%. Linear optical cavity 203 with a cavity size that may be set to roundtrip time on the order of 600 fs-1 ps. Pulse 214 is provided by a Ti:Sapphire femtosecond laser 202 of initial width 87 fs and wavelength 830 nm (with a band width of 11 nm). Pulse intensity 214 is split by a beam splitter 201 into pulse 214A and 214B. In this specific example, structure for time resolution 110 is referred to as a time microscope, which includes four parts.

The first part is a pump dispersion 212 that uses pulse 214A as input to create a resolving pulse 214C. The purpose of pump dispersion 212 is to produce resolving pulse 214C such that its frequency as a function of time is controlled and known so that a measurement of the frequency of the resulting output, i.e. pulse train 224, can be mapped onto the time domain. In the preferred embodiment of 200, resolving pulse 214C is a chirped pulse.

The second part is an input dispersion 218 that is used to disperse and chirp pulse 214B. The time delay resulting from input dispersion 218 is accomplished by positioning the grating of 218 and/or the length of the grating. The use of the input dispersion 218 makes it possible to overlap both in space and time the pulse train 216 produced by cavity 203 and chirped pulse 214C. Pulse train 216 and chirped pulse 214C will then arrive at the same time at the up-conversion BBO crystal 210.

BBO crystal 210, referred to as a nonlinear medium, is identified as the third part of the structure for time resolution 110. At 210, the intensities of the pulse train 216 and chirped pulse 214C are up-converted in time using sum-frequency generation resulting in radiation of half the wavelength, 415 nm (double the frequency) with an intensity distribution that is the product of the pulse train 216 and chirped pulse 214C intensities.

The fourth part is an output dispersion grating 222 that is used to disperse and re-phase the temporal image of the combined pulses 216 and 214C which creates pulse train 224. In this example, detector 112 includes two mechanisms for detecting the combined pulses 216 and 214C. A beam splitter 225 is used to split the intensity of the combined pulses to each detection mechanism. One mechanism of 112 is a streak camera 208 to collect the pulse train 224, magnified in time as a train of pulses. The other mechanism of 112 is a spectrometer 226 that is used to resolve the frequency of chirped pulse 214C along the amplitude profile.

Dynamics of Femtosecond Pulse-by-pylse Crds

Once the femtosecond laser pulse 201 is delivered, its intensity is split by beam splitter 201, directing half of the intensity in the form of pulse 214B to optical cavity 203 (using a steering mirror 205) and the other half in the form of pulse 214A to become chirped pulse 214C. Pulse 214A enters pump dispersion 212 which is a grating-dispersion delay line that stretches pulse 214A in the time domain and adds a linear frequency chirp to the pulse amplitude envelop creating chirp pulse 214C. The frequency chirp labels the amplitude profile of the pulse with a frequency so when it is dispersed by a spectrometer 226 the pulse train 224 has a frequency spectrum.

A pulse train 216 may be visualized within a single laser shot revealing individual pulses 214, which allow the pulse-by-pulse analysis to be performed. Similar to the description of FIG. 1, the pulse train 216 is created by a pulse 214B of light entering cavity 203 through the back of mirror 204, bouncing back and forth between mirrors 204 and 206, and on each bounce some light emerges through the opposite mirror 206. The losses of the cavity 203 cause the intensity of the light to decrease as a function of time creating a pulse train 216. When a sample is placed inside cavity 203, the intensity of the light constitutes additional losses due absorption by the sample at the wavelength of the light pulse radiation.

The pulse train 216 enters a similar dispersion grating 218 acting as a delay line. The chirped pulse 214C and the signal pulses 216 are overlapped in time and space on the surface of a BBO crystal 210 with the delay line allowing adjustment, by positioning grating of 218, to ensure the temporal overlap. The two signals are up-converted by sum-frequency generation. This arrangement produces a frequency-doubled pulse whose amplitude profile is a product of both the chirped pulse 214C and the signal pulse train 216. The resulting frequency-doubled radiation strikes an output dispersion grating 222 to form the temporal image of a pulse train 224 that has been magnified 100-fold in time.

The time microscope, as the structure for time resolution 110 in this specific embodiment, has a field of view or a record length of 10 ps, and the field of view can be moved along the pulse train 224 by changing the timing of the input delay line. The femtosecond pulse train 216 is visualized using the time microscope utilizing the principles of parametric temporal imaging which can magnify the time axis by a factor of 100 or more. Parametric temporal imaging is a nonlinear up-conversion technique that exploits the group dispersion properties of a light pulse to produce a temporal magnification, as is understood by those skilled in the art.

The pulse train 224 is detected in two parallel ways by detector 112, which detects time resolved response pulse train 224. Again, it is the goal of detector 112 to analyze each individual pulse response pulse 214B as it exited cavity 203 from the pulse train 224 in a time domain and/or in a frequency domain. The beam is split off by beam splitter 225 and enters a spectrometer 226 and a streak camera 228. The frequency chirped pulse 214C on the pulse 216 as in 224 provides a spectrum of frequencies along the amplitude profile that can be resolved in spectrometer 226. Second, a streak camera 228 collects the pulse train 224, magnified in time, as a train of picosecond pulses. The two techniques need to be calibrated to ensure a consistent time scale measurement. Further, the ring-down profile must be carefully extracted from the response function of each detector and the chirped pulse 214C profile to provide an accurate determination of the losses in the cavity.

The finite duration of the gaussian-shaped chirped pulse 214C limits the record length of the input to approximately 10 ps. In principal, data can be collected with only one pulse laser. In practice, the laser has a repetition rate of 80 MHz, and an image is averaged over one second.

The temporal resolution of the detection systems is determined by the image formation held in the phase information of the chirped signals. The output dispersion 222 produces peaks that are much narrower than those observed and the width, although not the shape of the peaks, may be determined by the resolution factor of the streak camera 208 or the spectrometer 226. Analysis of dispersion dynamics due to the sample will require this resolution factor to be considered. Such a resolution factor does not affect the principle of the analysis but would add a new consideration.

Figure 3:
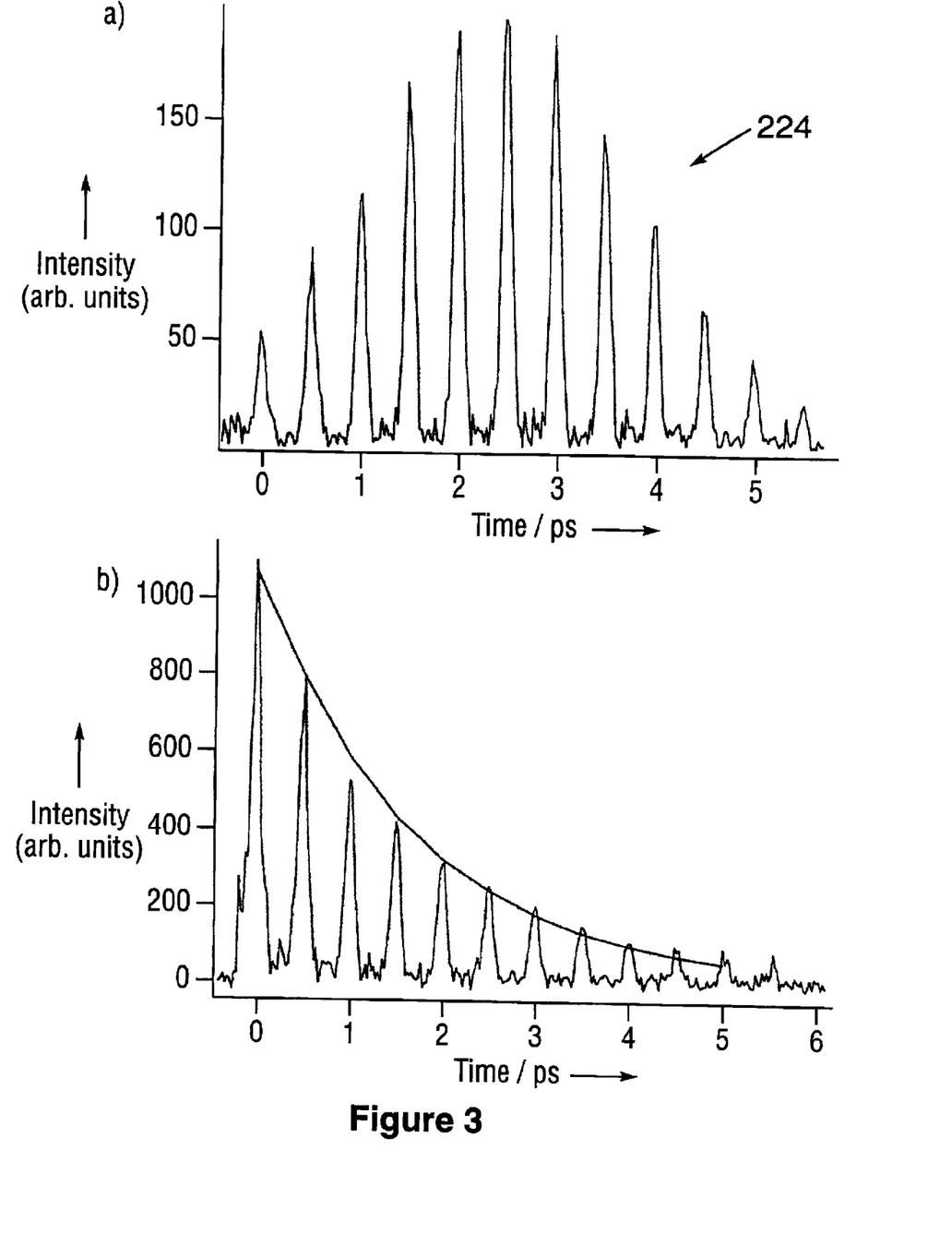
FIG. 3 illustrates a ring-down pulse profile obtained from an air-filled cavity (a) apodized with a gaussian time lens and (b) with apodization removed by normalization, for an empty 137 μm optical cavity.

FIG. 3a shows the pulse train image 224 from an air-filled 137 micron cavity using the pulse-by-pulse CRDS of 200. Since the chirped pulse 214C is approximately gaussian, there is an overall apodization to the sequence of pulses. This gaussian profile of pulse 214C can be accurately measured by scanning a single pulse 214 through the entire field of view and recording the amplitude profile. Once this profile is measured, this effect can be removed from all subsequent data. FIG. 3b shows the corrected data (i.e. in case apodization is removed from pulse train 224) in which the exponential decay is evident. The roundtrip time as measured from the spectrum is 932+/−4 fs. The pulses have a constant separation throughout the record length, which corresponds to a cavity length of 139+/−2 μm. This value agrees within 4% with that determined from the fringe spacings of optical cavity 203. This close agreement confirms the magnification of the time microscope to be a factor of 100, within the same error. The pulses will undergo dispersion due to the properties of the sample in the cavity as well as cavity mirrors. The roundtrip time is then a measure of the group velocity of each pulse after propagation through the cavity. The pulses also have increased width (127 fs) compared to the output of laser 202 (87 fs), which is constant over the pulse train. The observed increase is dominated by the dispersion of the pulse by the mirrors 204 and 206.

Figure 4:
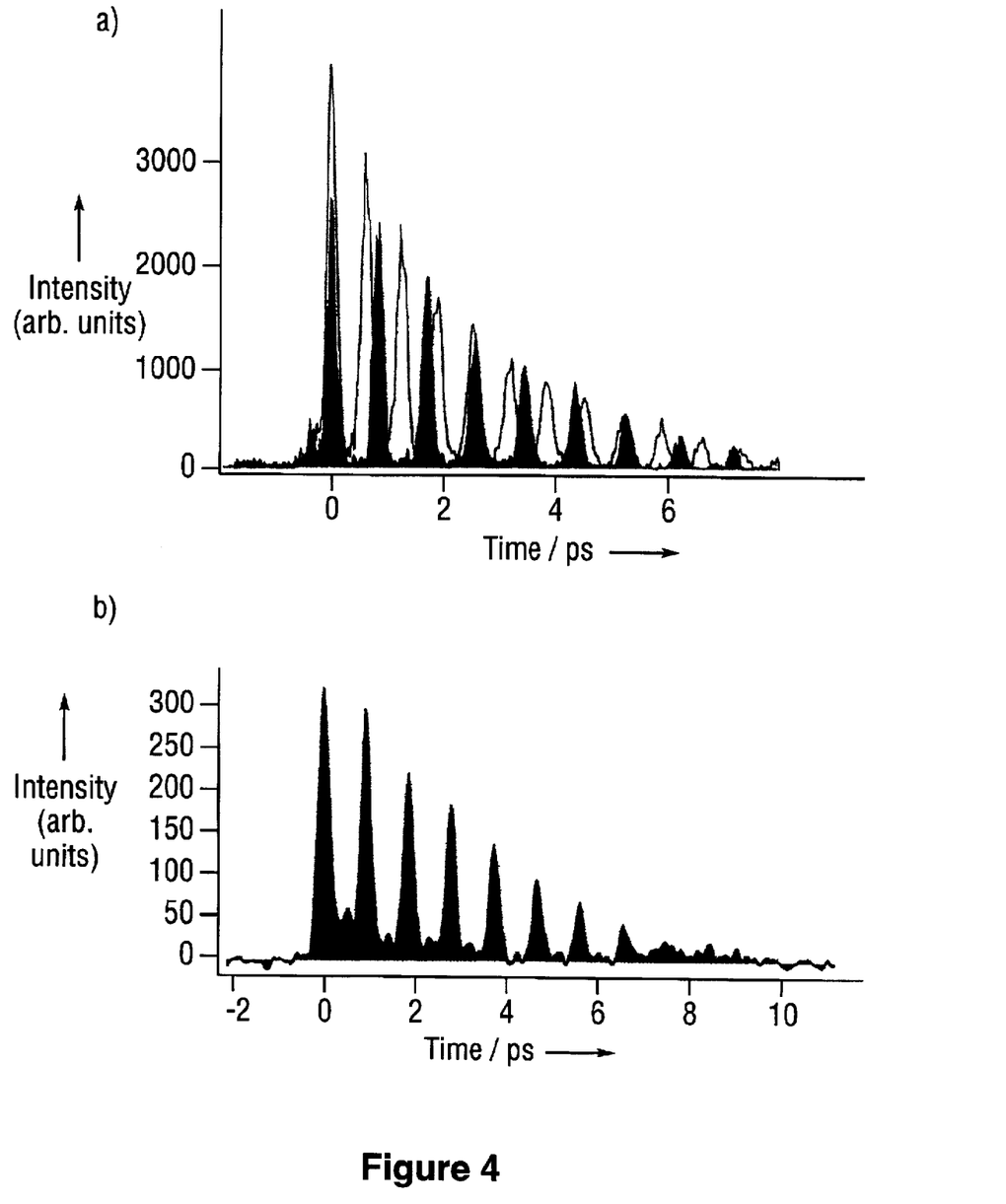
FIG. 4 illustrates a ring-down pulse profile obtained from two liquid samples, corrected for apodization, for a 95 μm optical cavity containing (a) ethanol, and (b) IR140 dye (19 nM) dissolved in ethanol. In each panel the corresponding ring-down profile for the empty cavity is shown as a solid line.

FIG. 4 shows the application of pulse-by-pulse CRDS according to 200 applied to liquid samples. Ethanol and a solution of the laser dye IR140 (19 nM) in ethanol were introduced separately into an empty cavity 203 with the resulting corrected pulse trains (i.e. in case apodization is removed from pulse train 224 which is plotted as a solid line) presented in FIGS. 4*a* and 4*b*, respectively. The roundtrip time is significant longer (852+/−7 fs) in the ethanol-filled cavity than that for empty cavity 203 (635+/−1 fs) owing to the refractive index of the solvent. The refractive index for ethanol may be determined by comparison of the roundtrip time for the empty cavity with the roundtrip time for the cavity containing ethanol, FIG. 4, and is measured as n=1.345+/−0.012 at 830 nm, compared with the value of n=1.3611 measured at 589 nm. Cavity 203 containing the dye solution also shows a different roundtrip tome corresponding to a refractive index of 1.313+/−0.024. The laser dye has a strong absorption at 830 nm and the change in the measured refractive index is a clear demonstration of the behavior for species that absorb at the frequency of the radiation.

Figure 5:
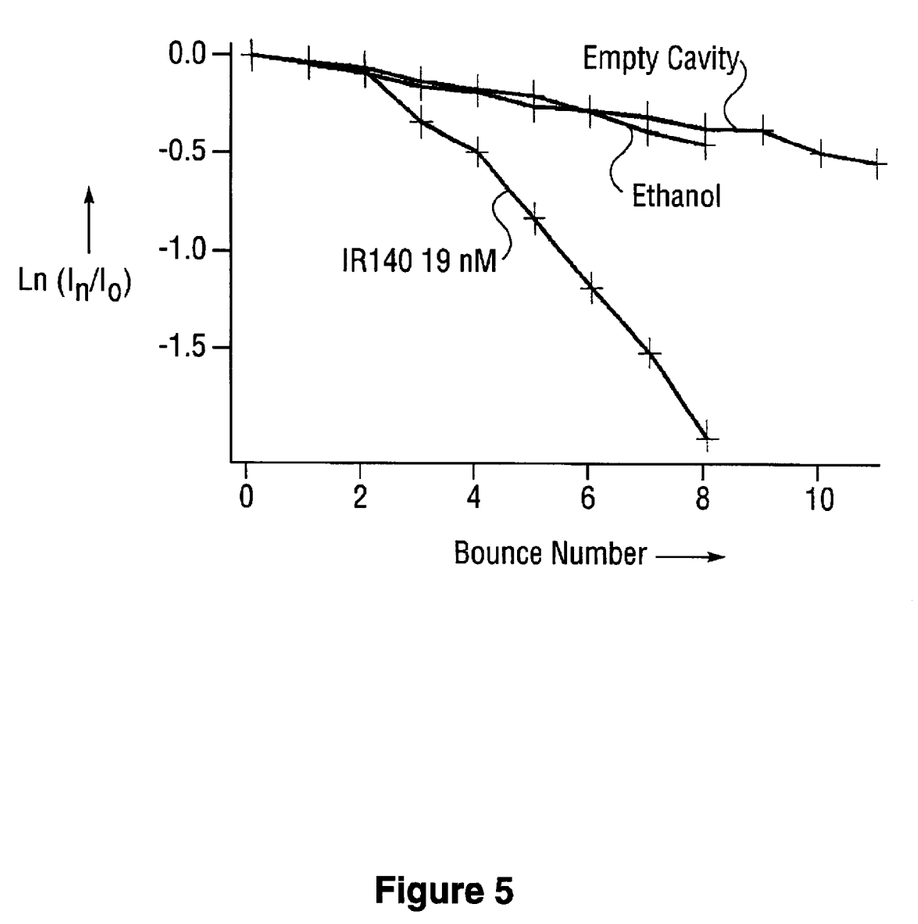
FIG. 5 illustrates a logarithmic plot of the relative ring-down pulse intensity of each pulse for an optical cavity filled with: ethanol, IR140 dye dissolved in ethanol, compared with the empty cavity.

FIG. 5 shows the variation of pulse intensity pulse-by-pulse according to 200, for an empty cavity, absorption due to ethanol and absorption due to IR140 dye. The logarithm of the normalized intensity of each pulse (In) with respect to the first intensity of the first pulse (Io) is plotted. In addition, the absorption of an empty cavity 203, which is the apodization produced by pulse 214C, has been plotted as the logarithm of the intensity of a pulse normalized to the intensity of the first pulse as a function of the number of pulses. An exponential decrease would appear as a straight line in this plot. The ring-down data is approximately exponential for ethanol, although it shows a slight curvature for the first few bounces. The decay for the dye solution, however, shows significant curvature and the ringdown is non-exponential.

Extensions and Advantages of Pulse-by-pulse Crds

The analysis of the pulse-by-pulse decay profile exploits the intrinsic insensitivity of the technique to variations in the light source 102 and 202. The rate of loss from cavity 103 and 203 at each bounce is controlled by the properties if the cavity defined by the mirrors as well as the sample within the cavity. This will be the same from laser pulse to laser pulse and will not suffer from light source noise interference. The analysis of the non-exponential decay is not limited by the need to fit data to multiple time scales with similar functional forms.

The dynamics of the sample in the presence of an intense laser field in the femtosecond laser pulse leads to the direct observation of non-linear absorption events in the sample which is not possible using conventional nanosecond sources or cavities constructed from high reflectivity mirrors. The ability to resolve each pulse in the ring-down profile eliminates the need for high reflectivity mirrors enabling broad band low reflectivity mirrors to be used. This opens the possibility of non-linear dynamics and absorption events to be observed directly.

Variations from the existing description involve the construction of cavity 103 and 203, and the implementation of the single-pulse detection technique. Cavity 103 or 203 may be non-linear, constructed from more than two mirrors in the form of a ring. In addition, the sample does not have to be within cavity 103 or 203 but has to be in optical contact with cavity 103 or 203. Here an optical element such as a prism may be placed within the cavity containing a surface at which total internal reflection (TIR) occurs. Associated with TIR is the formation of an evanescent wave in the lower refractive index medium. Absorption of radiation from the evanescent wave is observed as a loss in the cavity 103 or 203 and a consequent decrease in the ring-down time. This can be subjected to the same analysis as in the present invention. Both variations will benefit from the pulse-by-pulse analysis although the principles are exactly the same.

Furthermore, cavity 103 or 203 may be made from a solid material such as fiber optic, an optical micro-cavity or other light guiding device. Again, however, the pulse-by-pulse analysis remains the same. For these and similar cavities the material from which cavity 103 or 203 is constructed will add fixed absorption and scatter losses, which in addition to the presence of a sample, may result in short decay profiles. Here the pulse-by-pulse technique will be especially well-suited. Possibilities have been investigated with nanosecond and picosecond pulses, which could be readily detected as a single shot pulse train with streak camera 208 or a fast photo-multiplier tube.

The present invention also allows optical dense samples to be investigated over a broad range of wavelengths making available the sensitivity of CRDS to liquid- and solid-phase samples.

Furthermore, the same analysis of a non-exponential decay can be extended to include continuous wave (CW) laser sources as a light source 102 or 202. Here, light from a CW laser source is allowed to enter cavity 103 and 203 until it reaches a given intensity level. When this level is reached, the CW laser is shut off by a switching-off pulse, produced by a switching system. Subsequently the light in the cavity decays generating a CW ring-down profile. The same temporal imaging system as for pulse-by-pulse cavity ring-down described in the present invention may be used for detection of the CW ring-down by linking the timing of the resolving/chirped pulse to the switching-off pulse form the switching system. This could be a TTL pulse as part of a synchronizing timing circuit. Temporal resolution of a CW ring-down profile will yield similar information on the non-exponential decay dynamics. The analysis is enabled on the limit of temporal variation of detector 112. Both frequency and time domain measurements may be made as in the present invention.

Furthermore, using a continuous wave laser source, the analysis of pulse-by-pulse cavity ring-down spectroscopy could be extended and applied to cavity ring-up spectroscopy, whereby ring-up refers to the rate at which an optical cavity stores energy upon being irradiated.

It will be clear to one skilled in the art that the above embodiment may be altered in many ways without departing from the scope of the invention. For instance, it is obvious to one skilled in the art that the same method applies to ring-up spectroscopy as to ring-down spectroscopy. Accordingly, the following claims and their legal equivalents should determine the scope of the invention.

What is claimed is:

1. A pulse-by-pulse optical absorption apparatus, comprising:
   (a) a cavity;
   (b) a light source for delivering a pulse into said cavity;
   (c) a time resolving means for optically time resolving at least one response pulse produced by said cavity in response to said pulse; and
   (d) a detector for detecting an intensity of at least one time-resolved pulse produced by said time resolving means.

2. The pulse-by-pulse optical absorption apparatus of claim 1, wherein said light source is an ultra fast light source and said pulse is an ultra short pulse.

3. The pulse-by-pulse optical absorption apparatus of claim 1, wherein said at least one response pulse is at least one ultra short response pulse and said time resolving means is an ultra fast time resolving means.

4. The pulse-by-pulse optical absorption apparatus of claim 3, wherein said ultra fast time resolving means further comprises a nonlinear medium for mixing said at least one ultra short response pulse with a resolving pulse.

5. The pulse-by-pulse optical absorption apparatus of claim 4, wherein said resolving pulse is a chirped pulse.

6. The pulse-by-pulse optical absorption apparatus of claim 1, wherein said at least one response pulse is at least one ultra short response pulse and said detector is an ultra fast detector.

7. The pulse-by-pulse optical absorption apparatus of claim 1, wherein said at least one response pulse comprises a train of response pulses.

8. The pulse-by-pulse optical absorption apparatus of claim 7, wherein said detector further comprises a comparing device for comparing at least two said response pulses from said train of response pulses.

9. The pulse-by-pulse optical absorption apparatus of claim 1, wherein said cavity is a linear cavity with a predetermined cavity length set to resolve said at least one response pulse at said detector.

10. The pulse-by-pulse optical absorption apparatus of claim 9, wherein said cavity length is on the order of micrometers to set a time regime of said at least one response pulse on the order of femtoseconds.

11. The pulse-by-pulse optical absorption apparatus of claim 9, wherein said cavity length is on the order of millimeters to set a time regime of said at least one response pulse on the order of picoseconds.

12. The pulse-by-pulse optical absorption apparatus of claim 9, wherein said cavity length is on the order of meters to set a time regime of said at least one response pulse on the order of nanoseconds.

13. The pulse-by-pulse optical absorption apparatus of claim 9, wherein said cavity comprises at least one low reflector.

14. The pulse-by-pulse optical absorption apparatus of claim 1, wherein said cavity is a non-linear cavity with a predetermined cavity length set to resolve said at least one response pulse at said detector.

15. The pulse-by-pulse optical absorption apparatus of claim 14, wherein said cavity length is on the order of micrometers to set a time regime of said at least one response pulse on the order of femtoseconds.

16. The pulse-by-pulse optical absorption apparatus of claim 14, wherein said cavity length is on the order of millimeters to set a time regime of said at least one response pulse on the order of picoseconds.

17. The pulse-by-pulse optical absorption apparatus of claim 14, wherein said cavity length is on the order of meters to set a time regime of said at least one response pulse on the order of nanoseconds.

18. The pulse-by-pulse optical absorption apparatus of claim 14, wherein said non-linear cavity comprises at least one low reflector.

19. The pulse-by-pulse optical absorption apparatus of claim 1, wherein said cavity comprises an absorption sample whose absorption properties change in time.

20. A method for pulse-by-pulse optical absorption measurement, comprising the steps of:
  (a) providing a cavity;
  (b) delivering a pulse into said cavity;
  (c) optically time resolving at least one response pulse produced by said cavity in response to said pulse; and
  (d) detecting an intensity of at least one time-resolved response pulse.

21. The method of claim 20, wherein said step of delivering a pulse, comprises the step of:
  providing a means for delivering an ultra short pulse into said cavity.

22. The method of claim 21, wherein said step of time resolving said at least one response pulse, comprises the step of:
  time resolving at least one ultra short response pulse produced by said cavity in response to said ultra short pulse.

23. The method of claim 22, wherein said step of detecting said at least one response pulse comprises the step of:
  detecting said at least one ultra-short response pulse.

24. The method of claim 22, wherein said step of time resolving at least one response pulse comprises the step of:
  providing a nonlinear medium for mixing said at least one ultra short response pulse with a resolving pulse.

25. The method of claim 24, wherein said resolving pulse is a chirped pulse.

26. The method of claim 20, wherein said at least one response pulse is a train of response pulses.

27. The method of claim 26, wherein step of detecting further comprises the step of comparing at least two response pulses from said train of response pulses.

28. The method of claim 20, wherein said step of detecting further comprising the step of:
  providing an extracting means for analyzing said at least one response pulse.

29. The method of claim 20, wherein said step of providing a cavity, comprises the step of:
  providing a linear cavity with a predetermined cavity length set to resolve said at least one response pulse at said detector.

30. The method of claim 29, wherein said predetermined cavity length is on the order of micrometers to set a time regime of said at least one response pulse on the order of femtoseconds.

31. The method of claim 29, wherein said predetermined cavity length is on the order of millimeters to set a time regime of said at least one response pulse on the order of picoseconds.

32. The method of claim 29, wherein said predetermined cavity length is on the order of meters to set a time regime of said at least one response pulse on the order of nanoseconds.

33. The method of claim 29, wherein said step of providing a linear cavity,
  comprises the step of:
    providing at least one low reflector.

34. The method of claim 20, wherein said step of providing a cavity, comprises the step of:
  providing a non-linear cavity with a predetermined cavity length set to resolve said at least one response pulse at said detector.

35. The method of claim 34, wherein said predetermined cavity length is on the order of micrometers to set a time regime of said at least one response pulse on the order of femtoseconds.

36. The method of claim 34, wherein said predetermined cavity length is on the order of millimeters to set a time regime of said at least one response pulse on the order of picoseconds.

37. The method of claim 34, wherein said predetermined cavity length is on the order of meters to set a time regime of said at least one response pulse on the order of nanoseconds.

38. The method of claim 34, wherein said step of providing a linear cavity, comprises the step of:
  providing at least one low reflector.

39. The method of claim 20, further comprising the step of:
  providing a changing absorption sample within said cavity.

* * * * *